US010016306B2

(12) United States Patent
Sjöman

(10) Patent No.: US 10,016,306 B2
(45) Date of Patent: Jul. 10, 2018

(54) HEARING DEVICE CONTAINING HIDDEN FM-RECEIVER ANTENNA

(71) Applicant: 3M INNOVATIVE PROPERTIES COMPANY, St. Paul, MN (US)

(72) Inventor: Henrik J. Sjöman, Skillingaryd (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/510,446

(22) PCT Filed: Aug. 10, 2015

(86) PCT No.: PCT/US2015/044413
§ 371 (c)(1),
(2) Date: Mar. 10, 2017

(87) PCT Pub. No.: WO2016/039904
PCT Pub. Date: Mar. 17, 2016

(65) Prior Publication Data
US 2017/0246038 A1 Aug. 31, 2017

Related U.S. Application Data

(60) Provisional application No. 62/049,088, filed on Sep. 11, 2014.

(51) Int. Cl.
*A61F 11/14* (2006.01)
*H01Q 1/27* (2006.01)
*H04R 1/10* (2006.01)

(52) U.S. Cl.
CPC ............. *A61F 11/14* (2013.01); *H01Q 1/273* (2013.01); *H04R 1/1058* (2013.01); *H04R 1/1083* (2013.01); *H04R 2201/103* (2013.01)

(58) Field of Classification Search
CPC ..... A61F 11/14; H04R 1/1083; H04R 1/1058; H04R 2201/103; H01Q 1/273
See application file for complete search history.

(56) References Cited

U.S. PATENT DOCUMENTS

| 4,539,708 A * | 9/1985 | Norris .................... H04B 1/088 455/100 |
| 5,621,913 A | 4/1997 | Tuttle et al. |
| 2002/0080987 A1 | 6/2002 | Almqvist |

(Continued)

FOREIGN PATENT DOCUMENTS

| CN | 101202370 | 6/2008 |
| EP | 1002444 | 5/2000 |

(Continued)

OTHER PUBLICATIONS

International Search Report for PCT International Application No. PCT/US2015/044413, dated Sep. 24, 2015, 4 pages.

(Continued)

*Primary Examiner* — Brenda C Bernardi
(74) *Attorney, Agent, or Firm* — Christopher D. Karlen

(57) ABSTRACT

Hearing protection devices that contain an FM-receiver and antenna connected to one another, each being disposed interiorly in a protective muff of the hearing device, where the antenna is molded into a plastic housing in the protective muff are described, as are methods of making protective muffs used in such a device.

20 Claims, 3 Drawing Sheets

(56) References Cited

U.S. PATENT DOCUMENTS

| | | | |
|---|---|---|---|
| 2002/0135519 A1 | 9/2002 | Luch | |
| 2004/0005071 A1* | 1/2004 | Siskin | A61F 11/14 381/378 |
| 2004/0056818 A1 | 3/2004 | Sledkov | |
| 2010/0119076 A1* | 5/2010 | Monk | A61F 11/14 381/71.6 |
| 2010/0273441 A1* | 10/2010 | Dubash | H01Q 1/243 455/192.2 |
| 2013/0028456 A1 | 1/2013 | He | |
| 2013/0076573 A1* | 3/2013 | Rappoport | H01Q 1/243 343/702 |

FOREIGN PATENT DOCUMENTS

| | | | |
|---|---|---|---|
| EP | 1002444 A1 * | 5/2000 | |
| EP | 1469623 A2 * | 10/2004 | |
| RU | 118189 | 7/2012 | |
| WO | WO 1995-26117 | 9/1995 | |
| WO | WO 9526117 A1 * | 9/1995 | |
| WO | 2009/131518 | 10/2009 | |

OTHER PUBLICATIONS

Broadcast FM Radio Receiver for Consumer Electronics Si4704/05-D50, Silicon Laboratories, 2010, URL: https://www.silabs.com/documents/public/data-sheets/Si4704-05-D50.pdf.

* cited by examiner

HEARING DEVICE CONTAINING HIDDEN FM-RECEIVER ANTENNA

FIELD

The present description relates to a hearing device that includes an FM-Receiver.

BACKGROUND

Hearing protectors, including hearing protectors that include muffs to be worn over the ears of a user, are well known. Some hearing protectors additionally include an FM-receiver to allow for FM-radio listening functionality in a hearing protector. Generally, hearing protectors that include FM-receiver must also include an antenna. By far the most common antenna for use in such a construction is a "whip antenna." Whip antennas generally protrude from the hearing protector, often times in an upward direction, and create drawbacks.

SUMMARY

In one aspect, the present description relates to a hearing protection device. The hearing protection device includes a first protective muff that is to be placed over a user's ear. The protective muff includes an FM-receiver, a metal antenna and a plastic housing. The FM-receiver is disposed interiorly in the protective muff. The metal antenna is also disposed interiorly in the protective muff and is connected to the FM-receiver. The metal antenna is secured by being molded into the plastic housing. At least one connection point to the antenna protrudes from the plastic housing.

In another aspect, the present description relates to a method of making an earmuff for use in a hearing protection device. The method includes the steps of melting a metal into an elongated mold and cooling in order to create an antenna, placing the antenna into a mold for molding a plastic housing, injection molding the second mold with plastic material, resulting in the antenna being embedded in the plastic material, with the exception of two protruding attachment pieces from the antenna, and connecting at least one of the attachment pieces to an FM-receiver by soldering the attachment piece and FM-receiver to a common circuit board.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
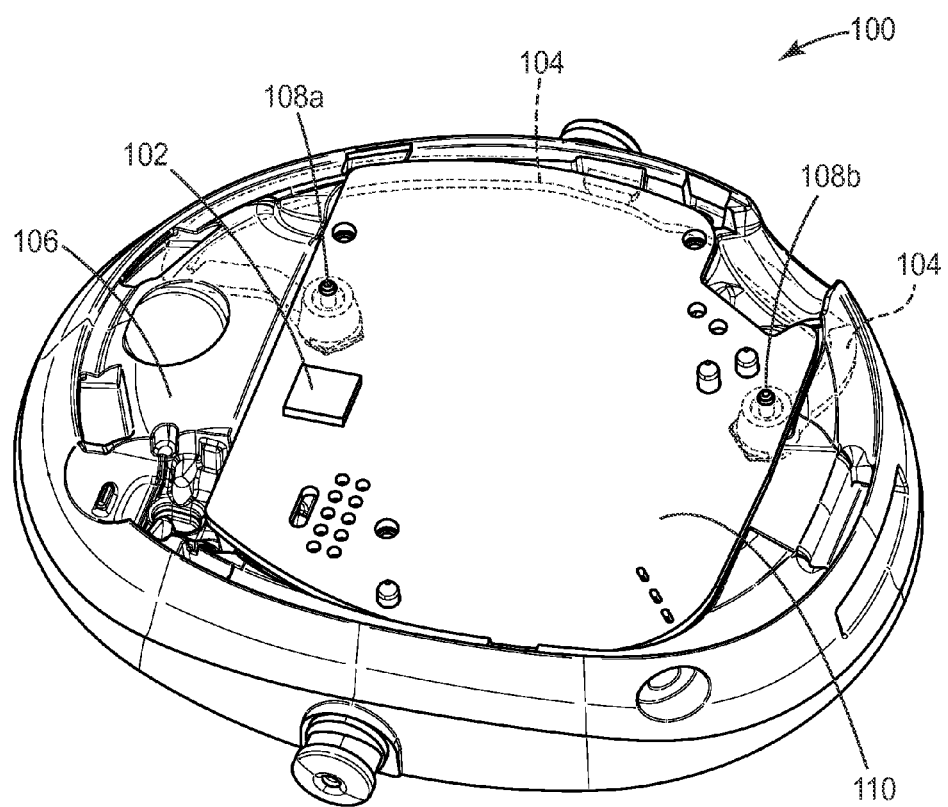
FIG. 1 is a perspective view of a protective muff according to the present description.

In the following detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as forming a "coincident interface" with, or being "on," "connected to," "coupled with," "stacked on" or "in contact with" another element, component or layer, it can be directly on, directly connected to, directly coupled with, directly stacked on, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example.

As noted previously, today, most hearing protectors that include FM-receivers also include a "whip antenna." Whip antennas generally protrude from the hearing protector, often times in an upward direction, and create certain problems. For example, where hearing protectors with a whip antenna are being worn in a work environment, as they often are, the whip antenna can sometimes get in the way, and prohibit a worker from moving freely. Additionally, whip antennas are often damaged in the work environment due to their exposed location. The need to attach the rather large whip antenna to the muff of a hearing protector may require one to create muffs having greater profiles. Finally, whip antennas are generally attached to the FM-receiver after the muff itself is produced, thereby requiring additional processing steps to create the final product.

The presently described invention solves each of these problems. The description provides for a hearing device that contains a "hidden" FM-receiver antenna. This hidden antenna is protected from exposure to the work environment elements, and does not require additional space on the surface of the muff for mounting, allowing for a lower profile earmuff. Additionally, the antenna can be assembled in-line during the production of the hearing protection device, eliminating the necessity of additional manufacturing steps. It therefore offers a major improvement over known technologies in the art.

FIG. 1 illustrates a protective muff used in a hearing protection device of the present description. First protective muff 100 is intended for placement over the user's ear. Beneath the surface of the muff that is opposite the surface that will be in directly contact with the user's head are a number of elements. First protective muff includes an FM-receiver 102, in this embodiment, an FM-receiver chip. First protective muff further includes a metal antenna 104 that is disposed interiorly in the protective muff and is connected to the FM-receiver. Protective muff also includes a plastic housing 106. Plastic housing may be any appropriate type of plastic, including ABS plastic. The metal antenna 104 is secured by being molded into the plastic housing 106. However, at least one connection point to the antenna, such as first connection point 108a, protrudes from the plastic housing. The metal antenna may also have a second connection point 108b that protrudes from the plastic housing. Either protrusion may be used to connect to the FM-receiver.

Were one to attempt to embed a conventional FM-antenna into the cup of a hearing protection muff, it is inevitable that the antenna would be too short in regard to the FM-band frequency. The middle of the FM band is at about 100 Mz and to make the antenna itself resonate at this frequency would require an antenna length of at least around 75 cm (assuming a quarter wavelength antenna). One could coil the antenna to improve the slack issues in the muff and improve the issue, and in fact such coiling is typically what is done with typical whip antennas today. However, to ensure that the antenna is short enough to fit in the muff, and not require the use of a whip antenna, another solution must be used, as described with respect to antenna 104 further below.

In certain embodiments, it is desirable for the FM-receiver to be a receiver with capability to change its input capacitance. One appropriate FM-receiver for use in the presently described device is the IC Si4704 receiver from Silicon Laboratories, Inc. (Austin, Tex.). This receiver has an antenna input that can actively change its input capacitance, in order to create electrical resonance at the tuned frequency. Since the antenna is electrically short it has a low radiation resistance and is capacitive rather than inductive. Accordingly, to tune the antenna to the FM-band, one has to add an inductor to the antenna to make it resonate somewhere in the middle of the FM-band. This creates a very narrow frequency range where the antenna reception is good, but creates issues for listening to other frequencies across the FM-band not in this narrow range. The ability of the receiver to change input capacitance at the antenna allows it to move the resonance to a tuned station, despite the fixed inductance of the circuit.

Another way to compensate for the narrow frequency range and low radiation resistance of a short antenna—without using a radio receiver with an adaptable input capacitance—is to use a low noise amplifier (LNA). An LNA is often used to amplify radio frequency signals. An example of such a component is BGB719N7ESD from Infineon Technologies (Neubiberg, Germany). The LNA can be placed between the antenna and the FM-receiver circuit and amplifies radio signals at frequencies outside the resonance frequency of the antenna and its resonant inductor that normally would be too weak to receive.

Antenna 104 of the present description may be a metal antenna. In some embodiments the antenna may be made up of a lightweight, low resistivity metal, such as zinc or aluminum. As noted above, one characteristic of the antenna is that it is much shorter than conventional antennas for FM-receivers. In fact, the antenna of the present description generally has a length that is at least 20 times shorter than the shortest FM wavelength that the FM-receiver receives.

As noted above, first protective muff includes a metal antenna 104 that is disposed interiorly in the protective muff and is connected to the FM-receiver 102. Metal antenna may be connected to the FM-receiver through any appropriate means. In one embodiment, the metal antenna is connected to the FM-receiver through a circuit board 110. As shown in FIG. 1, the circuit board may be soldered to the metal antenna 104 at first connection point 108a, and also be soldered to the FM-receiver 102, creating the connection between the FM-receiver and antenna. The circuit board, in this embodiment, is placed on top of the plastic housing 106 and secured to the housing using screws.

Figure 2:
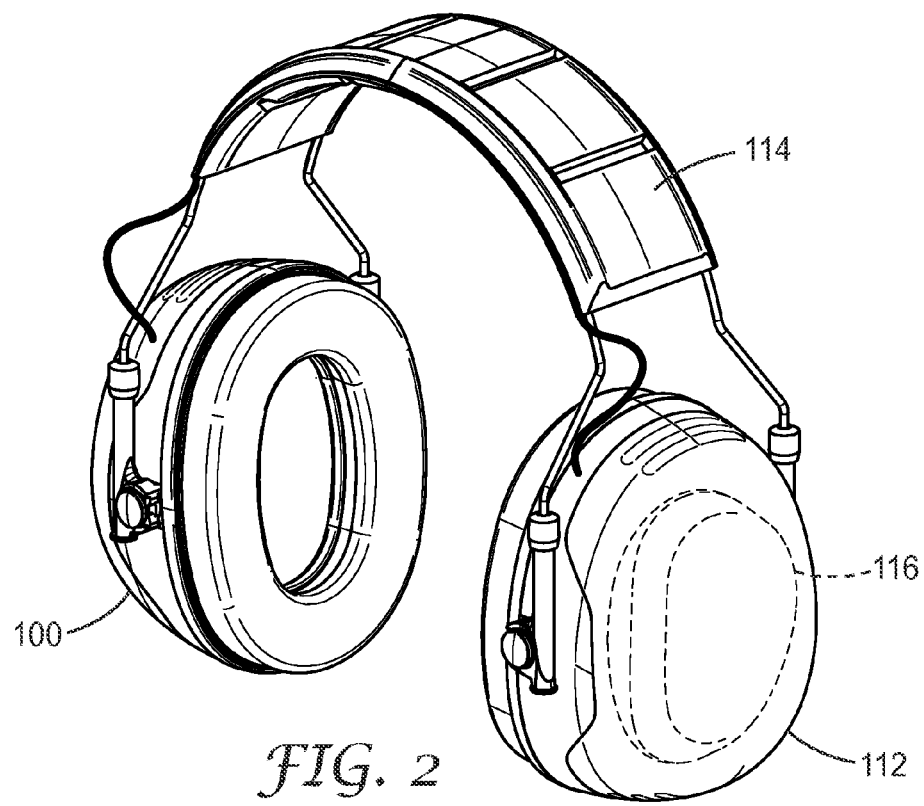
FIG. 2 is a perspective view of a hearing protection device according to the present description.

The hearing protection device of the present description, which includes the first protective muff described above, may further include a second protective muff. FIG. 2 illustrates such a hearing protection device. Second protective muff 112 is connected to first protective muff 100 by a bridging portion 114. Second protective muff 112 may house a power supply 116 that supplies power to the FM-receiver 102. In one embodiment, the power supply may be alkaline batteries, though other appropriate power supplies could potentially be used. Power travels from the second protective muff 112 to the first protective muff by traveling over the bridging portion 114.

Figure 3A:
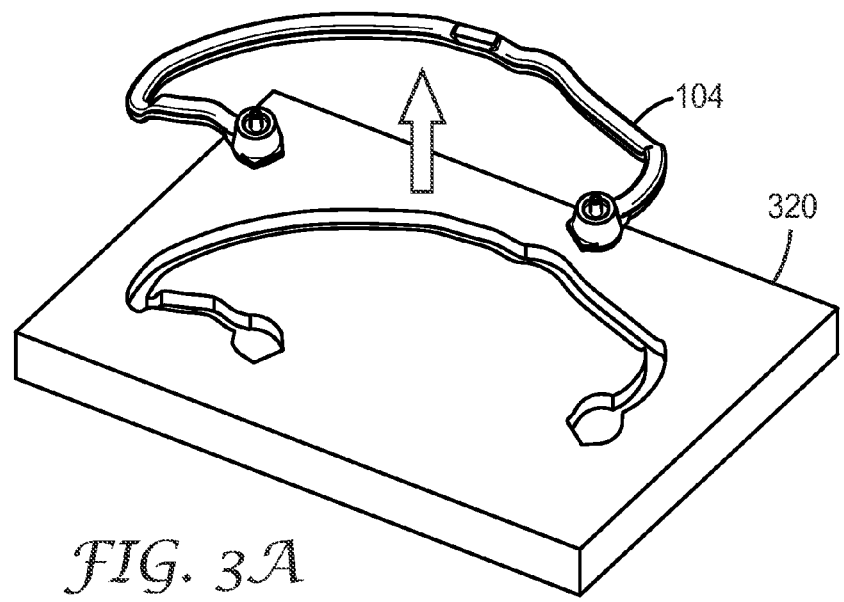
FIGS. 3*a*-3*c* illustrate a method of making a protective muff according to the present description.
Figure 3B:
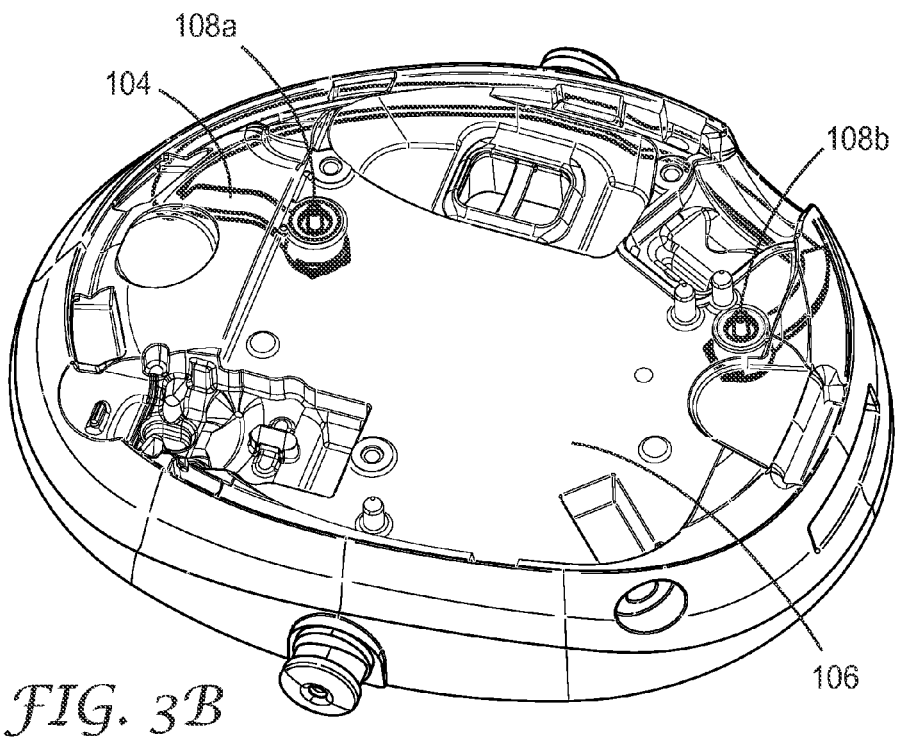
Figure 3C:
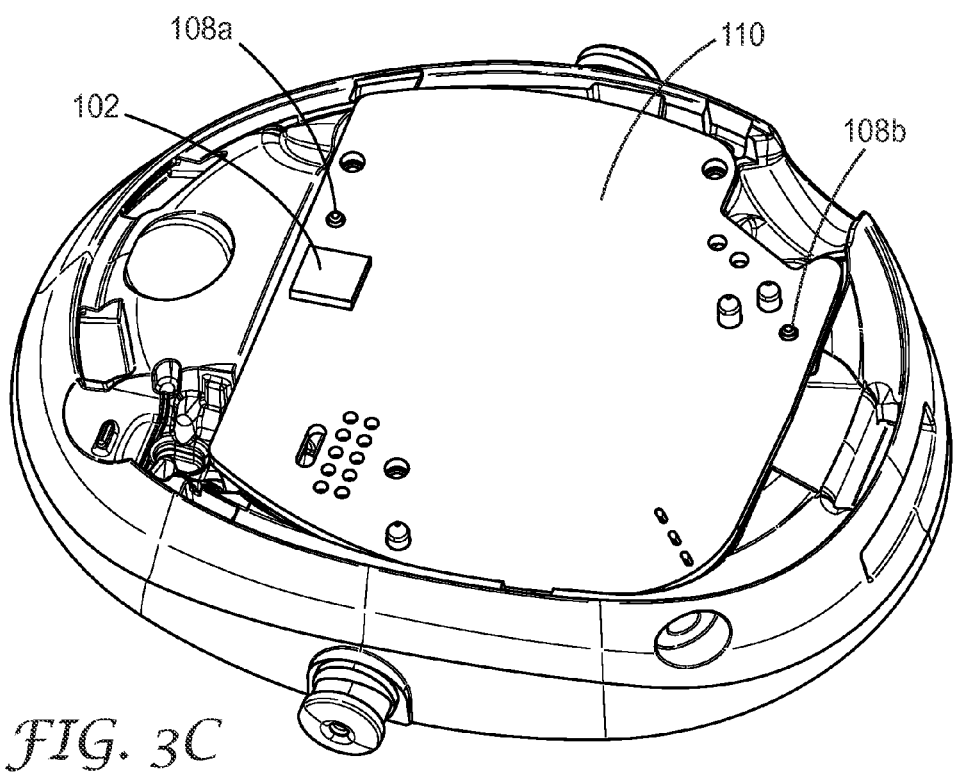

FIGS. 3a-3c provide illustrations of a method of making an earmuff for use in a hearing protection device, according to the present description. The method includes a first step of melting a metal into an elongated mold 320, and cooling. As noted above, particularly appropriate metals include ones that are lightweight, and have low resistivity, such as aluminum or zinc. Once cooled, the metal has been molded into an antenna 104, which can be removed from the mold. These steps are illustrated in FIG. 3a. The antenna 104 may then be placed into a mold for injection molding the plastic housing of the earmuff. Next, the mold for injection molding the plastic housing of the earmuff is injection molded with plastic material, resulting in the antenna 104 being embedded in the plastic housing 106, with the exception of two protruding attachment pieces from the antenna 108a and 108b (as shown in FIG. 3b). Next, a circuit board 110 may be applied over the plastic housing, such that antenna attachment pieces 108a and 108b also protrude from the common circuit board (as shown in FIG. 3c). Finally, at least one of the attachment pieces 108a or 108b is connected to an FM-receiver 102 by soldering the attachment piece and FM-receiver to a common circuit board 110.

What is claimed is:

1. A hearing protection device, comprising:
   a first protective muff to be placed over a user's ear, the protective muff comprising:
      a plastic housing extending between a first end region and a second end region opposite of the first end region;
      an FM-receiver disposed interiorly in the protective muff;
      an FM-receiving antenna also disposed interiorly in the protective muff and connected to the FM-receiver, the FM-receiving antenna comprising a molded metal body molded into the plastic housing, the molded metal body extending from a first end to a second end and comprising at least one connection point that protrudes from the plastic housing.

2. The hearing protection device of claim 1, wherein the metal body comprises a lightweight, low resistivity metal.

3. The hearing protection device of claim 2, wherein the metal comprises zinc or aluminum.

4. The hearing protection device of claim 1, wherein the FM-receiving antenna has a length that is at least 20 times shorter than the shortest FM wavelength that the FM-receiver receives.

5. The hearing protection device of claim 1, wherein a circuit board is soldered to the connection point, and also soldered to the FM-receiver, creating the connection between the FM-receiver and FM-receiving antenna.

6. The hearing protection device of claim 1, wherein a second connection point to the FM-receiving antenna protrudes from the plastic housing.

7. The hearing protection device of claim 1, further comprising a second protective muff to be placed over a user's other ear, the second protective muff being connected to the first protective muff by a bridging portion.

8. The hearing protection device of claim 7, wherein the second protective muff houses a power supply, and the FM-receiver is powered by power traveling from the second protective muff over the bridging portion to the first protective muff.

9. The hearing protection device of claim 1, wherein the FM-receiver is capable of changing its input capacitance.

10. The hearing protection device of claim 1, further comprising a low noise amplifier.

11. The hearing protection device of claim 10, wherein the low noise amplifier is positioned between the FM-receiver and the FM-receiving antenna.

12. The hearing protection device of claim 1, wherein the FM-receiving antenna is not coiled.

13. The hearing protection device of claim 1, wherein the molded metal body extends from the first end region to the second end region of the plastic housing.

14. The hearing protection device of claim 1, wherein the first end comprises a first connection point and the second end comprises a second connection point, the first and second connection points protruding from the plastic housing.

15. The hearing protection device of claim 14 further comprising a circuit board, wherein the first and second connection points are connected to the circuit board by soldering.

16. The hearing protection device of claim 1, wherein the plastic housing has a contoured shape and wherein the molded metal body has a shape that follows the contoured shape of the plastic housing.

17. A method of making an earmuff for use in a hearing protection device, comprising:
    melting a metal into an elongated mold and cooling in order to create an antenna,
    placing the antenna into a mold for injection molding the plastic housing of claim 1,
    injection molding the plastic housing with plastic material, resulting in the antenna being embedded in the plastic housing, with the exception of two protruding attachment pieces from the antenna, and
    connecting at least one of the attachment pieces to an FM-receiver by soldering the attachment piece and FM-receiver to a common circuit board.

18. The method of claim 17, wherein the metal comprises a lightweight, low resistivity metal.

19. The hearing protection device of claim 18, wherein the metal comprises zinc or aluminum.

20. The hearing protection device of claim 17, further comprising the step of applying the circuit board on top of the plastic housing, such that the two attachment pieces also protrude from the circuit board, before the FM-receiver and at least one of the two attachment pieces are soldered to the circuit board.

* * * * *